United States Patent [19]

Webster et al.

[11] Patent Number: 5,313,825
[45] Date of Patent: May 24, 1994

[54] DUAL MASS DYNAMIC CONE PENETROMETER

[75] Inventors: Steve L. Webster, Vicksburg; Thomas P. Williams, Port Gibson, both of Miss.

[73] Assignee: The United States of Americas as represented by the Secretary of the Army, Washington, D.C.

[21] Appl. No.: 880,264

[22] Filed: May 8, 1992

[51] Int. Cl.$^5$ .............................................. G01N 3/42
[52] U.S. Cl. .......................................... 73/81; 73/84
[58] Field of Search .................... 73/81, 82, 83, 84, 85, 73/12.13

[56] References Cited

U.S. PATENT DOCUMENTS

| | | | |
|---|---|---|---|
| 2,892,344 | 6/1959 | Sklar | 73/83 |
| 2,938,377 | 5/1960 | Sklar | 73/83 |
| 4,332,160 | 6/1982 | Baragar et al. | 73/84 |
| 4,398,414 | 8/1983 | MacGregor | 73/84 |

FOREIGN PATENT DOCUMENTS

| | | | |
|---|---|---|---|
| 187159 | 10/1922 | United Kingdom | 73/84 |
| 595191 | 11/1947 | United Kingdom | 73/82 |

OTHER PUBLICATIONS

*Transportation Research Record* 1192, Chua eta l., 1988, "Dynamic Analysis Using the Portable Pavement Dynamic Cone Penetrometer", pp. 27–28 only.
Proc., 6th Intl. Conf. on Structural Design and Asphalt Pavements, Livneh et al., Jul. 1987, "Pavement and Material Evaluation . . . ".
*The Rhodesian Engineer*, vol. 7, No. 5, pp. 852–854, Van Vuuren, "Rapid Determination of CBR with the Portable Dynamic Cone . . . ".

*Primary Examiner*—Robert Raevis
*Attorney, Agent, or Firm*—Luther A. Marsh

[57] ABSTRACT

The invention is a dynamic cone penetrometer for measuring soil shear strength which includes an elongated cylindrical rod having a tip end and a handle end. An anvil portion is mounted to the rod at a selected distance from the handle and a penetrometer tip having a conical free end is secured to the tip end of the rod for engaging the soil or sample. A two weight drop hammer having a cylindrical through bore is slidably mountable on the rod at the handle end for striking the anvil with a selected force when released from a fixed distance from said anvil. The drop hammer is formed in two parts including a cylindrical core portion of a first diameter, and a cylindrical support portion extending from the core portion to a second diameter. The second weight has a through bore and is sleevable over the core for engaging and resting upon the support portion. A releasable fastener secures the second weight to the core so that proper measurements may be performed with the first weight alone for weak soils or with both weights for stronger soils and surfaces. The penetrometer tip may be disposable and releasably secured to the tip end of the rod.

13 Claims, 2 Drawing Sheets

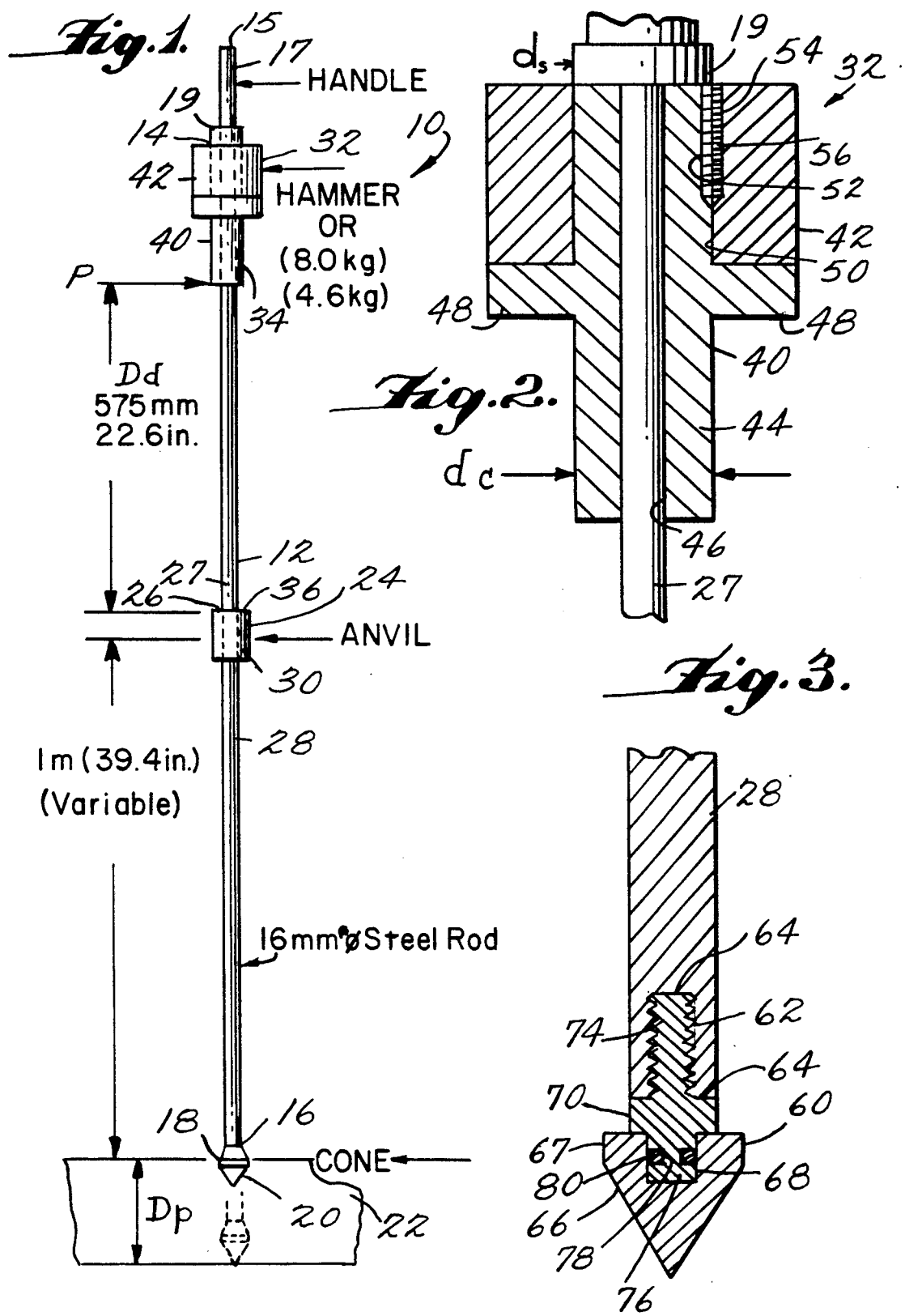

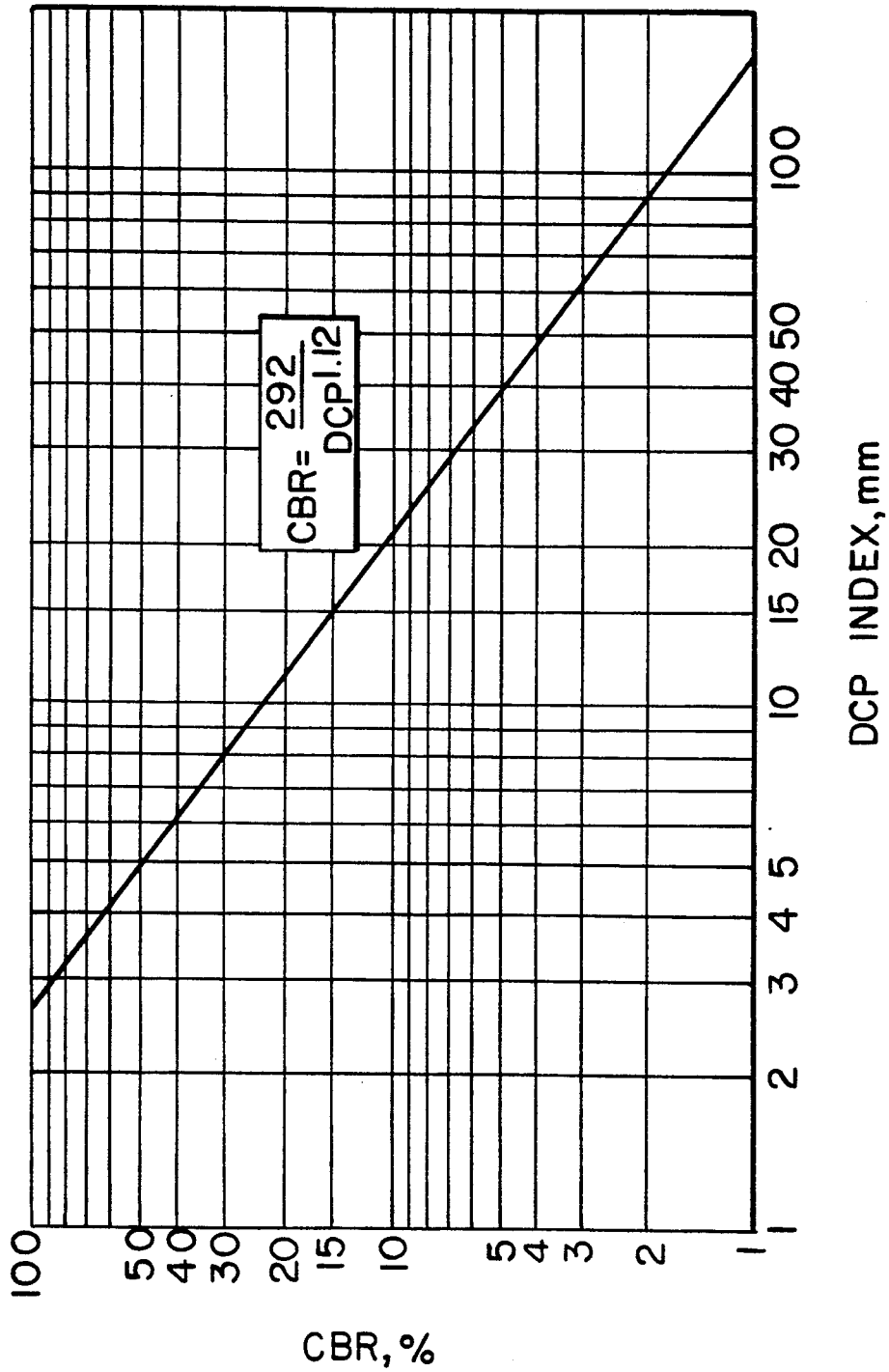
Fig. 4. CORRELATION OF CBR VERSUS DCP INDEX

DUAL MASS DYNAMIC CONE PENETROMETER

BACKGROUND OF THE INVENTION

The invention pertains to a device for testing the shear strength of soils. In particular, the invention pertains to a penetrometer useful for both high strength granular road and airfield pavement layers and relatively weak underlying subgrade type soils.

One of the most important soil properties is shearing resistance or shear strength which is related to the ability of the soil to withstand a load. This is especially important in relation to the supporting strength or bearing capacity of a soil used as a base or subgrade beneath a road, runway or other structure.

For most military applications, the well known California Bearing Ratio (CBR) value of a soil is used as a measure of shear strength. The CBR is determined by a penetration shear test and is used with empirical curves for designing and evaluating unsurfaced, aggregate surfaced and flexible pavements for military roads and airfields. The CBR test is usually performed on laboratory-compacted test specimens. When used on-sight for pavement evaluations, destructive test pits are dug to determine pavement layer thickness. Field or on-sight CBR tests are conducted on the base course, the sub-base, and sub-grade materials. On-sight CBR tests are time consuming to run and are generally not practical for use in a theater of operations.

For unsurfaced roads and airfields, a known airfield cone penetrometer is used to determine index of soil strengths (airfield index). The airfield penetrometer consists of a 30° cone with a 0.2 square inch base area. The force required to penetrate to various depths in the soil is measured by a spring, and the airfield index is read directly from the penetrometer. The airfield cone penetrometer has a range of 0-15 which corresponds to a CBR value of approximately 0-18. While the device is compact, sturdy and simple enough to be used by military personnel experienced in soil strength determination, a major drawback of the airfield cone penetrometer is that it will not penetrate various types of crusts or thin base course layers that may overlie softer layers. Relying only on the surface airfield index test could, under some conditions, result in the loss of a vehicle or an aircraft.

Another device for measuring shear strength is a single mass dynamic cone penetrometer. The device has only a single heavy mass designed to penetrate strong soils up to a CBR of 100. It cannot, however, measure the strength of very weak soil layers for example, CBR less than 1. Also, the single heavy mass penetrometer is too heavy to accurately measure the strength of clay soils having a CBR of 10 or less. The single mass device may also penetrate thin crust layers in less than one hammer drop, and actually measure the average strength of the weak and crust layers instead of the actual strength of each layer.

There are known devices which use a single mass and conical penetrometer tips of various kinds. See for example, Chua et al., *Transportation Research Record* 1192, 1988, which shows a single mass device with an attached scale. Livneh et al, Proc., 6th International Conference on Structural Design of Asphalt Pavements, Jul. 1987, shows a single weight penetrometer with a 30° cone. Van Vuuren, *The Rhodesian Engineer*, vol. 7, no. 5, pp 852-854, shows a single weight device (10 Kg) with a 460 mm drop height. None of the references show devices which conveniently produce desirable results for both the weak and strong soil conditions.

SUMMARY OF THE INVENTION

The present invention eliminates the disadvantages and shortcomings of the described prior arrangements. In a particular embodiment, the invention comprises a dynamic cone penetrometer for measuring soil shear strength. The device includes an elongated cylindrical rod having a tip end and a handle end. An anvil portion is mounted to the rod at a selected distance from the handle end. A penetrometer tip having a conical end is secured to the tip end of the rod for engaging the soil or sample and a handle is secured to the handle end. A calibrated drop weight having a cylindrical through bore is slidably mounted on the rod between the handle and the anvil for striking the anvil with a selected force when released from the handle end. The drop weight comprises a first weight, including a cylindrical core portion of a first diameter, and a cylindrical support portion extending from the core portion to a second diameter. The second weight has a through bore and is sleevable over the handle and the core for engaging and resting upon the support portion. A releasable fastener secures the second weight to the core so that measurements may be performed using the first weight alone for weak soils or with both weights for stronger soils and surfaces.

BRIEF DESCRIPTION OF THE DRAWINGS

FIG. 1 is a side elevation of the present invention for use on a soil sample with penetration of the device into the soil sample shown in phantom view;

FIG. 2 is a side sectional elevation of the dual mass drop weight or hammer for use in the penetrometer in the present invention;

FIG. 3 is a side sectional elevation of a disposable cone and adapter for use in an alternative embodiment of the present invention; and FIG. 4 is a calibration curve illustrating CBR vs. core penetration index.

DESCRIPTION OF THE PREFERRED EMBODIMENT

In accordance with one embodiment of the invention, FIG. 1 illustrates a dual mass dynamic cone penetrometer 10. The device includes a cylindrical rod 12 having a handle end 14 and a tip end 16. A handle 15 is threadably secured to the rod 12 at the handle end 14 and a conical penetrometer tip 18 is threadably secured at the tip end 16 as illustrated. The penetrometer tip 18 has a conical end 20 for engaging a soil sample 22 to be tested. An anvil 24 is secured at a fixed position relative to the handle end 14 and has a striker surface 26. The handle 15 has a grip portion 17 and a stop portion 19, the stop 19 has a diameter $d_s$ which is greater than the grip portion 17. In the embodiment illustrated, the rod 12 is formed in detachable sections including a drop rod 27 and a gauge rod 28 which are threaded in abutting relationship within a threaded bore 30 of the anvil 24 as illustrated. The anvil 24 may be welded to the gauge rod 28.

A hammer 32 has an internal through bore 34 and is sleeved over the drop rod 27 as illustrated between the stop 19 and the anvil 24. The hammer 32 is freely slidable, and with the rod 12 upright, when the hammer 32 is dropped from a position in abutment with the stop 19 the hammer falls a fixed drop distance $D_d$ of 575 millimeters measured between the bottom of the hammer 32 and the striker surface 26 of, the hammer 32 strikes the striker surface 26 of the anvil 24 causing the penetrometer tip 18 to penetrate the soil sample 22 to a depth $D_p$ as illustrated.

The hammer 32 comprises a first weight 40 of about 4.6 kilograms and a second weight of about 3.4 kilograms. As illustrated in FIG. 2, the first weight 40 includes a cylindrical core 44 having a central through bore 46 for slidably receiving the drop rod 27 therein. The first weight 40 also has a support portion 48 which extends outwardly in a radial direction as illustrated. The core 44 has a diameter $d_c$ which is the same as the diameter $d_s$ of the stop 19. The second weight 42 is formed of an annular cylinder having a central bore 50. The second weight 42 is sleevable over the core 44 and stop 19 and rests on the support 48 as illustrated. The core 44 has a threadably, semicircular keyway 52 formed in an outer wall thereof and the second weight 42 has a threaded axial semicircular keyway 54 in an inner wall therein. The semicircular keyways 52 and 54 may be circumferentially aligned and a set screw 56 may be threaded therein for locking the second weight 42 in position with respect to the first weight 40.

In accordance with the invention, when a relatively hard or strong soil sample 22 is to be tested, the hammer 32 including the first and second weights 40 and 42 are secured together for a combined hammer weight of about 8 kilograms and employed to perform a drop test. In those situations where the soil sample 22 is relatively weak, the second weight 42 is removed from the hammer 32 and the drop test is performed with the first weight 40 only of 4.6 kilograms. Using the first weight portion only imparts a penetration force on the tip end which is approximately one half the penetration force imparted by the combined hammer weight of the first and second weight portions. Drop test results, namely penetration per blow for each drop test measurement, may be correlated with the California Bearing Ratio (CBR) standard in accordance with the expression:

$$CBR = \frac{292}{DCP^{1.12}}$$

where CBR is the California Bearing Ratio and DCP is the dynamic cone penetration index in millimeters per blow.

FIG. 4 illustrates a calibration curve for DCP index versus CBR in percent. In the present invention, when the hammer 32 includes the combined weight of the first and second weights 40 and 42, the DCP index is calculated as the average penetration per blow in millimeters using the combined weight hammer 32. When only the first weight 40 is used, the DCP index is calculated as two times the average penetration per blow of the reduced weight hammer 32. The same correlation curve for DCP index versus CBR in percent can be used with either hammer weight.

In accordance with an embodiment of the invention, FIG. 3 illustrates a disposable cone penetrometer tip 60. In the arrangement, the gauge rod 28 has a threaded axial hole 62 in the lower end 64. The disposable penetrometer tip 60 includes a conical portion 66, a circular base portion 67 and an axial aperture 68 therein. An adapter 70 has a threaded tail portion 74 which is threadably secured in a threaded axial bore 62 of the rod 28. Likewise, the adapter 70 has a cylindrical nose portion 76 which has an annular slot 78 therein. An elastomeric O-ring 80 is secured in the slot 78 and the nose portion 76 of adapter 70 is secured in the bore 68 by interference with the O-ring 80. After a drop test, the gauge rod 28 and adapter 70 may be easily removed from the ground by an upward pull whereby the nose portion 76 disengages from the bore 68 in the tip 66 which is left in the soil sample.

The penetrometer as illustrated in FIG. 1 has a gauge rod 28 with a diameter $d_r$ which is less than the base diameter $d_t$ of the penetrometer tip 18 or the circular base portion 67 of the disposable penetrometer tip 60 in FIG. 3. The rod 28 diameter $d_r$ is 16 millimeters and the base diameter of the penetrometer tips 18 or 60 is 20 millimeters. The difference of 4 millimeters between the rod diameter $d_r$ and the conical tip diameter $d_t$ helps to ensure that the resistance to penetration is exerted on the cone and not the rod.

In the embodiments of the invention, the gauge rod 28 and various tip portions 18 and 66 are lubricated with oil especially in clay soils or the like. In the hammer present invention, the first weight portion is 4.6 kilograms and the hammer second weight portion is 3.4 kilograms. The drop distance $D_d$ is 575 millimeters. The gauge distance from the tip 18 to the anvil 24 is 1 meter to provide for a sufficient number of drop test measurements to be made in sequence. A minimum penetration depth $D_p$ of about 25 millimeters is required before the penetrometer reading can be considered reliable. Several hammer drops may be required before the minimum 25 millimeter penetration depth reading is reached. The dynamic cone penetration index for the measured penetration depth is based on the average penetration in millimeters per blow.

While there has been described what at present are considered to be the preferred embodiments of the invention, it will be apparent to those skilled in the art that various changes and modifications may be made therein without departing from the invention. Accordingly, it is intended in the appended claims to cover such changes and modifications as common within the true spirit and scope of the invention.

What is claimed is:

1. A dynamic cone penetrometer for measuring soil shear strength comprising:
   an elongated cylindrical rod having a tip end and a handle end;
   an anvil portion mounted to the rod at a selected distance from the handle end;
   a penetrometer tip secured to the tip end of the rod and having a conical free end for engaging the soil; and
   a two weight drop hammer having a cylindrical through bore and being slidably mounted on the rod at the handle end for striking the anvil with a selected force when released from a fixed distance above said anvil, said hammer comprising a first weight portion including a cylindrical core portion of a first diameter and support portion extending radially therefrom and a second weight portion having a through bore and being sleevable over the core for engaging the support portion and fastener means for releasably securing the second weight portion from the first weight portion so that drop measurements may be performed with the first weight portion for relatively weak soils and with the first and second weights secured together for relatively strong soil.

2. The penetrometer of claim 1, wherein the penetrometer tip includes releasable fastener means for releasably interconnecting the penetrometer tip with the rod.

3. The penetrometer of claim 2, wherein the releasable fastener means includes an adapter having a threaded tail end and being threadably secured in an axial aperture in the tip end of the rod and a forward end for frictionally engaging an axial aperture in the penetrometer tip.

4. The penetrometer of claim 3, wherein the forward end of the adapter is a cylindrical portion having an annular groove formed therein and an elastomeric O-ring located within the groove, the axial aperture in the disposable penetrometer tip mounts on the forward end of the adapter and is secured in position by friction with the O-ring.

5. The penetrometer of claim 1, wherein the hammer has a combined weight of about 8 kilograms and the first weight is about 4.6 kilograms.

6. The penetrometer of claim 5, wherein the first weight portion imparts a penetration force on the tip end which is approximately one half the penetration force imparted by the combined weight of the first and the second weight portions.

7. The penetrometer of claim 1, wherein the hammer imparts a penetration force in accordance with the relation:

$$CBR = 292/DCP^{1.12}$$

where CBR is a California Bearing Ratio and DCP is the penetration index of a tip relative to the soil surface.

8. The penetrometer of claim 1, wherein the core portion and the second weight portion have alignable threaded axial apertures therein; and the securing means comprises a set screw threadably securable in the axial apertures when aligned.

9. The penetrometer of claim 1, wherein the tip has an angle of about 60° and a circular base diameter of about 20 millimeters.

10. The penetrometer of claim 1, wherein the fixed distance is 575 millimeters.

11. The penetrometer of claim 1, wherein the distance between the anvil and the penetrometer tip is about 1 meter.

12. The penetrometer of claim 1, wherein the rod has a diameter less than the diameter of the conical tip.

13. The penetrometer of claim 1, further comprising a handle grip at the handle end, said handle grip having a stop end for engaging the hammer, the stop end of the handle having a diameter corresponding to the diameter of the core portion of the hammer for allowing the second weight to be unsecured and sleeved from the core portion of the hammer over the handle into the core.

* * * * *